April 12, 1966
C. H. FISCHER
GLADIOLUS PLANT
Filed Oct. 16, 1964
Plant Pat. 2,620
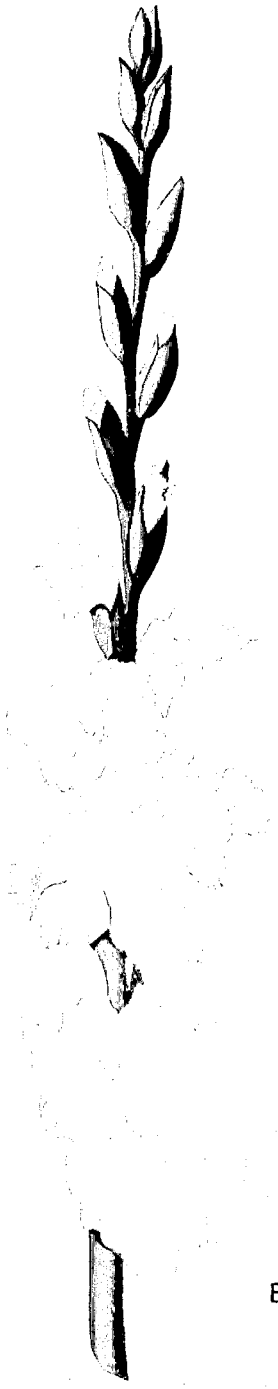
INVENTOR
Carl H. Fischer
By: Lamont Johnston
ATTORNEY United States Patent Office Plant Pat. 2,620
Patented Apr. 12, 1966

2,620
GLADIOLUS PLANT

Carl H. Fischer, St. Charles, Minn., assignor to Selected Glads, Inc., New Albany, Ind., a corporation of Tennessee Filed Oct. 16, 1964, Ser. No. 404,543
1 Claim. (Cl. Plt.—85)

My new invention relates to a new and improved variety of gladiolus and is notable particularly for its small size, unusual green and orange color combination, robust health and ability to perform well in all parts of the United States. I have identified this new variety as seedling #670–58 in my breeding work.

To the best of my knowledge, this variety is the result of a cross derived from mixed stock, both on the seed parent and pollen parent. Hand cross polenization was done by me in my field at St. Charles, Minnesota but no precaution was taken to prevent admixture by bees or insects.

This new variety has been asexually reproduced by me in Minnesota and California by natural increase from cormels through several generations and its characteristics have proven to be permanently fixed.

The illustration, made a part of this application, shows a single bloom spike, reduced in size, and is as nearly true to color as it is possible to depict. The illustration shows the color, form and spike formation.

In the following detailed description, color plate reference are to "The Horticultural Colour Chart" by the British Colour Council. Where there are other references to color, the ordinary dictionary meanings of the terms are intended.

*The plant*

Growth: Vigorous; grows to 40 inches in height over-all. Excellent propagator.

Blooming: Blooms in 65 to 70 days from large bulbs in the North.

Stems: Slender, ¼ to 5/16 inch in diameter. Color of stem is rose above the bulb.

Foliage: Deep green, upright. Leaves are 1½ inches wide. Plant foliage, excluding the flower spike, is 24 to 26 inches tall.

Disease resistance: Excellent resistance to known gladiolus diseases.

Corms: Very smooth, fine-husked, round with a pinkish tinge to husk. Corms are well-covered by the husk. Flesh is Salmon 412/1.

*The flower*

Spike: Flowerhead is 16 inches in length, with sixteen to eighteen buds of which seven to eight open at one time.

Bud:

*Size.*—Opening buds are 1¾ inches long.

*Opening.*—Five to six show color at one time.

Flower:

*Arrangement.*—Florets are informally placed on the spike.

*Size.*—Individual florets are 2¾ to 3¼ inches in diameter.

*Form.*—Hooded, ruffled, somewhat triangular.

*Keeping qualities.*—Exceptional opener from tight bud.

Petals:

*Shape.*—Upper petals are incurved; all are ruffled and fluted.

*Size.*—Upper petal is 1½ inches across; lip petal is 1 inch.

*Aspect.*—Heavy substance.

*Fragrance.*—None.

*Color.*—Outer edges and upper petal are Saturn Red 13/1. Throat is Chartreuse Green 663. There is a rose hairline in the calyx at base of upper petals.

Reproductive organs:

*Stamens.*—Cream; purple pollen.

*Pistils.*—Cream.

*Comparisons*

My new variety resembles Green Elf (unpatented), more than any other variety but differs from it principally as follows:

(1) This variety is more ruffled.
(2) It has a high order of beauty.
(3) It has rounder florets.
(4) It has a sharper contrast of green and orange.

Having thus disclosed my invention, I claim:

The new and distinct variety of gladiolus plant, substantially as herein shown and described, characterized by its green and orange blossom color combination, small size and vigorous health.

No references cited.

ABRAHAM G. STONE, *Primary Examiner.*

R. E. BAGWILL, *Assistant Examiner.*